(12) United States Patent
Kuellmer et al.

(10) Patent No.: US 10,398,473 B2
(45) Date of Patent: Sep. 3, 2019

(54) DEVICE FOR BRACING VERTEBRAE OF THE HUMAN SPINAL COLUMN

(71) Applicant: GEBR. BRASSELER GMBH & CO. KG, Lemgo (DE)

(72) Inventors: Michael Kuellmer, Lemgo (DE); Frank Hagemann, Lemgo (DE)

(73) Assignee: GEBR. BRASSELER GMBH & CO. KG, Lemgo (DE)

( * ) Notice: Subject to any disclaimer, the term of this patent is extended or adjusted under 35 U.S.C. 154(b) by 0 days.

(21) Appl. No.: 15/525,797

(22) PCT Filed: Jun. 29, 2015

(86) PCT No.: PCT/EP2015/064685
§ 371 (c)(1),
(2) Date: May 10, 2017

(87) PCT Pub. No.: WO2016/074808
PCT Pub. Date: May 19, 2016

(65) Prior Publication Data
US 2018/0153583 A1 Jun. 7, 2018

(30) Foreign Application Priority Data
Nov. 12, 2014 (DE) .......................... 10 2014 223 112

(51) Int. Cl.
*A61B 17/70* (2006.01)
(52) U.S. Cl.
CPC ........ *A61B 17/7005* (2013.01); *A61B 17/701* (2013.01); *A61B 17/7002* (2013.01);
(Continued)

(58) Field of Classification Search
CPC ............ A61B 17/7005; A61B 17/7002; A61B 17/7004; A61B 17/701; A61B 17/7032; A61B 17/7037
(Continued)

(56) References Cited

U.S. PATENT DOCUMENTS 5,697,929 A  12/1997 Mellinger
7,641,674 B2  1/2010 Young
(Continued)

FOREIGN PATENT DOCUMENTS

DE  9202745  4/1992
DE  69206318  7/1996
(Continued)

OTHER PUBLICATIONS

German Office Action dated May 21, 2015 from counerpart German Patent Application No. DE 10 2014 223 112.4.
(Continued)

*Primary Examiner* — Pedro Philogene
*Assistant Examiner* — David C Comstock
(74) *Attorney, Agent, or Firm* — Shuttleworth & Ingersoll, PLC; Timothy Klima (57) ABSTRACT

A device for bracing the vertebrae of the human spinal column, having at least one pedicle screw with a head that is formed so as to be at least partially spherical and that is received into an at least partially spherical mounting area of a pedicle head, wherein the pedicle head has a centric recess which includes the mounting area and a slit for receiving a rod that is arranged transversely with respect to the centric recess, as well as an internal thread which is formed inside the centric recess opposite the mounting area and inside of which a safety screw for clamping the rod is arranged, wherein the safety screw is provided with an anti-rotation device at that side that is facing towards the rod.

14 Claims, 15 Drawing Sheets

(52) U.S. Cl.
CPC ...... *A61B 17/7004* (2013.01); *A61B 17/7032* (2013.01); *A61B 17/7037* (2013.01)

(58) Field of Classification Search
USPC ................................ 606/261, 264, 267, 270
See application file for complete search history.

(56) References Cited

U.S. PATENT DOCUMENTS

| | | | |
|---|---|---|---|
| 2003/0187433 A1 | 10/2003 | Lin | |
| 2005/0228385 A1* | 10/2005 | Iott | A61B 17/7032 606/278 |
| 2006/0217716 A1 | 9/2006 | Baker et al. | |
| 2007/0233086 A1* | 10/2007 | Harms | A61B 17/7002 606/273 |
| 2012/0035670 A1 | 2/2012 | Jackson et al. | |
| 2012/0046699 A1* | 2/2012 | Jones | A61B 17/7037 606/305 |
| 2012/0083850 A1 | 4/2012 | Kaufman et al. | |
| 2012/0165875 A1 | 6/2012 | Drewry et al. | |
| 2014/0188172 A1* | 7/2014 | Nichols | A61B 17/7004 606/278 |
| 2014/0214097 A1 | 7/2014 | Jackson et al. | |

FOREIGN PATENT DOCUMENTS

| | | |
|---|---|---|
| DE | 19951145 A1 | 5/2001 |
| EP | 0870474 A1 | 10/1998 |
| EP | 1808141 A1 | 7/2007 |
| FR | 2950243 A1 | 3/2011 |
| WO | WO9116020 A1 | 10/1991 |
| WO | WO9220294 A1 | 11/1992 |
| WO | WO9311715 A1 | 6/1993 |
| WO | WO9426191 A1 | 11/1994 |

OTHER PUBLICATIONS

International Search Report and Written Opinion dated Sep. 9, 2015 from counterpart PCT Application No. PCT/EP2015/064685.

* cited by examiner

DEVICE FOR BRACING VERTEBRAE OF THE HUMAN SPINAL COLUMN

This application is the National Phase of International Application PCT/EP2015/064685 filed Jun. 29, 2015 which designated the U.S.

This application claims priority to German Patent Application No. 102014223112.4 filed Nov. 12, 2017, which application is incorporated by reference herein.

What is known from DE 92 02 745 U1 is a device for bracing vertebrae of the human spinal column, having at least two pedicle screws with a ring-shaped head which has a slit that continuous towards the opening and comprises internal thread sections. A safety screw can be screwed into the slit, thus securing a rod that can be inserted into the slit inside the head of the pedicle screw.

WO 94/26191 shows an osteosynthesis device with a bone screw, in particular a pedicle screw, with a fork head that has a groove as well as a correcting rod that is supported inside the groove of the fork head and that is secured against any rotation by a structuring on its outer surface.

Another such device is shown in DE 692 06 318 T2. Further reference is made to WO 93/11715 A1, WO 92/20294 A1, WO 91/16020 A1, and DE 92 02 745 U1.

When it comes to such devices for bracing vertebrae that are inserted internally, that is, inside the body of the patient, it is necessary to take measures to ensure that the settings of the device as preselected by the operating surgeon are permanently maintained and are not changed due to movements of the body.

The invention is based on the objective to create a device of the above-mentioned kind for bracing vertebrae of the spinal column that has a high degree of dimensional stability and is secured against any loosening or displacement of individual structural components while at the same time having a simple structure and being easy and operationally safe to use.

The objective is achieved by a combination of features disclosed herein, the disclosure showing further advantageous embodiments.

Thus, the invention shows a device for bracing vertebrae of the human spinal column, having at least one pedicle screw, with its head being embodied so as to be at least partially spherical and being received inside an at least partially spherical mounting area of a pedicle head, wherein the pedicle head has a centric recess that comprises the mounting area, and a slit that is arranged transversely with respect to the centric recess and serves for receiving a rod, as well as an internal thread that is formed inside the centric recess opposite the mounting area and inside of which a safety screw for clamping the rod is arranged, wherein the safety screw is provided with an anti-rotation device at that side that is facing towards the rod.

Thus, the invention provides a construction in which a safety screw is screwed into a pedicle head in order to clamp a rod. The rod is received inside a slit of the pedicle head and is pretensioned against the end of the slit of the pedicle head by means of the safety screw.

When the spinal column moves, it may occur that the safety screw is loosened and the rod is thus no longer sufficiently secured at the pedicle head and thus at the pedicle screw. To avoid that, the anti-rotation device according to the invention is provided. In a preferred embodiment of the invention, it comprises elevations and convex areas that are arranged substantially radially at the front side of the safety screw. Thus, the safety screw catches on the surface area of the rod, whereby any unintentional loosening of the safety screw is avoided. Thus, according to the invention, a form-fit meshing between the front-side surface of the safety screw and the surface area of the rod is provided. This form-fit catching can be easily realized if the safety screw is screwed in with a corresponding force and the elasticity of the used materials is taken into consideration. However, a pretension is present in the mounted state, reliably avoiding any unintentional rotation of the safety screw thanks to the form-fit catching between the front-side surface and the rod.

According to the invention, the front-side surface of the safety screw can be provided with elevations and concave areas of different designs, for example with multiple divisions, so that—as viewed with respect to the rotational axis of the safety screw—radial elevations and radial concave areas are formed in a star-shaped manner around the circumference of the front side. The structuring of these elevations and concave areas can be embodied in a rounded manner, but it is also possible to provide them with a trapezoid cross-section, with a bulge-like cross-section, chamfered, or triangular cross-section.

In order to achieve a safe catching as well as a safe rotation prevention by means of the safety screw, it is provided in an advantageous further development of the invention that the surface area of the rod is embodied so as to be smooth or roughened up or structured. In a smooth embodiment, the rod can mesh with the form-fit radial elevations or radial concave areas of the safety screw in a safe manner. In an embodiment where the surface area is roughened up, an additional friction force is created, leading to an additional or supplementary form-fit catching with the safety screw. Further, it is possible to embody the rod in a non-rounded manner, and to form profiled or flattened areas at its surface area, for example.

In the following, the invention is explained based on exemplary embodiments in connection with the drawing. Herein.

Figure 1:
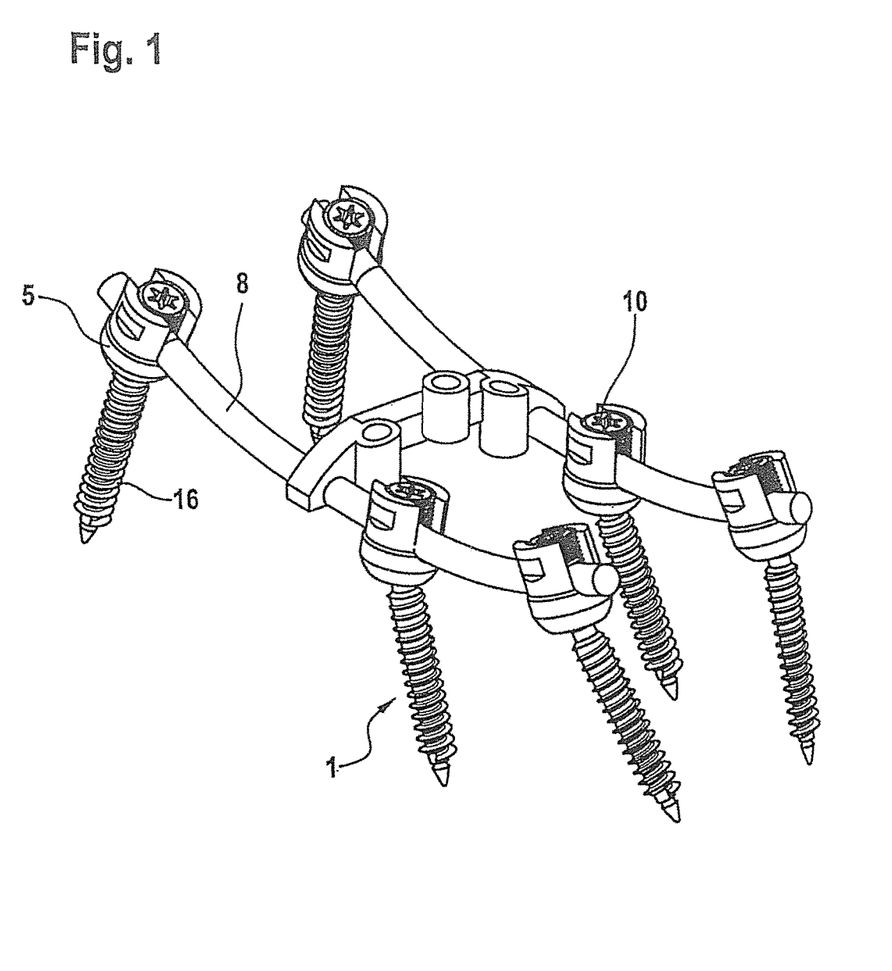
FIG. 1 shows a perspective view of a device according to the invention in the mounted state.
Figure 9:
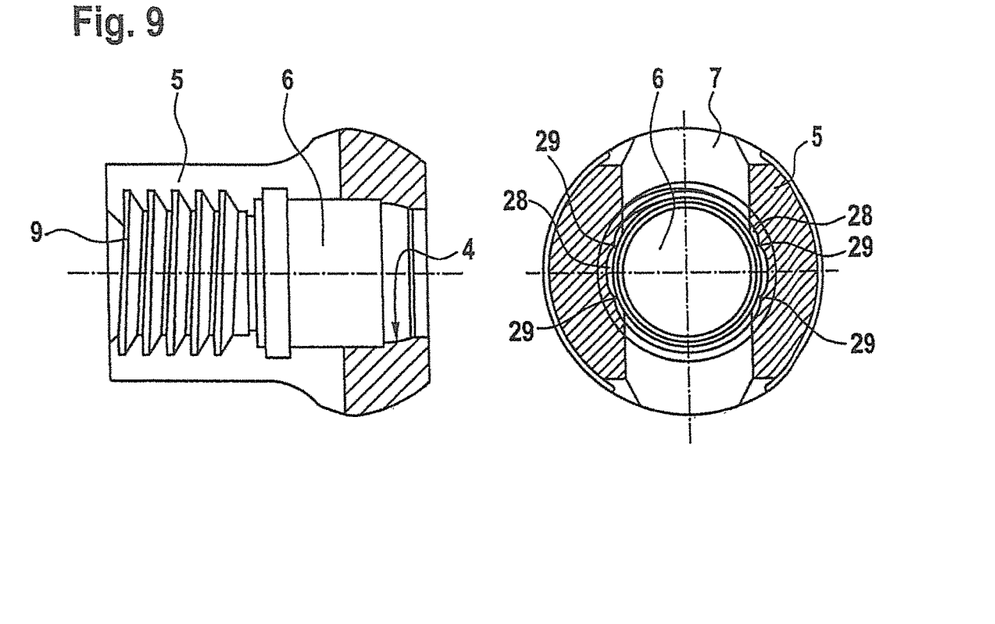
FIGS. 9, 10 show an axial partial section view as well as a lateral view and a front-side sectional view of a pedicle head according to the invention.

FIG. 1 shows a perspective rendering of a device according to the invention in the mounted state, with multiple pedicle screws 1 being shown that are oriented in different directions, as it occurs when they are screwed into a spinal column. The pedicle screws are provided with a thread 16, as will be described in the following in particular in connection with FIG. 11. At their upper end, the pedicle screws have a head 2 (see FIG. 11) that is provided with a spherical area 3. The pedicle screws 1 are passed through a centric recess of a pedicle head 5, respectively. The pedicle head 5 has a slit 7 into which a rod 8 is inserted. The latter is clamped by means of a safety screw 10, the thread of which meshes with an internal thread 9 of the pedicle head 5. The internal thread 9 is formed in a centric recess 6 (see FIG. 9) of the pedicle head 5. What results from the embodiment of the safety screw 10 according to the invention is a form-fit catching with the rod 8, as will be described in detail in the following.

Figure 2:
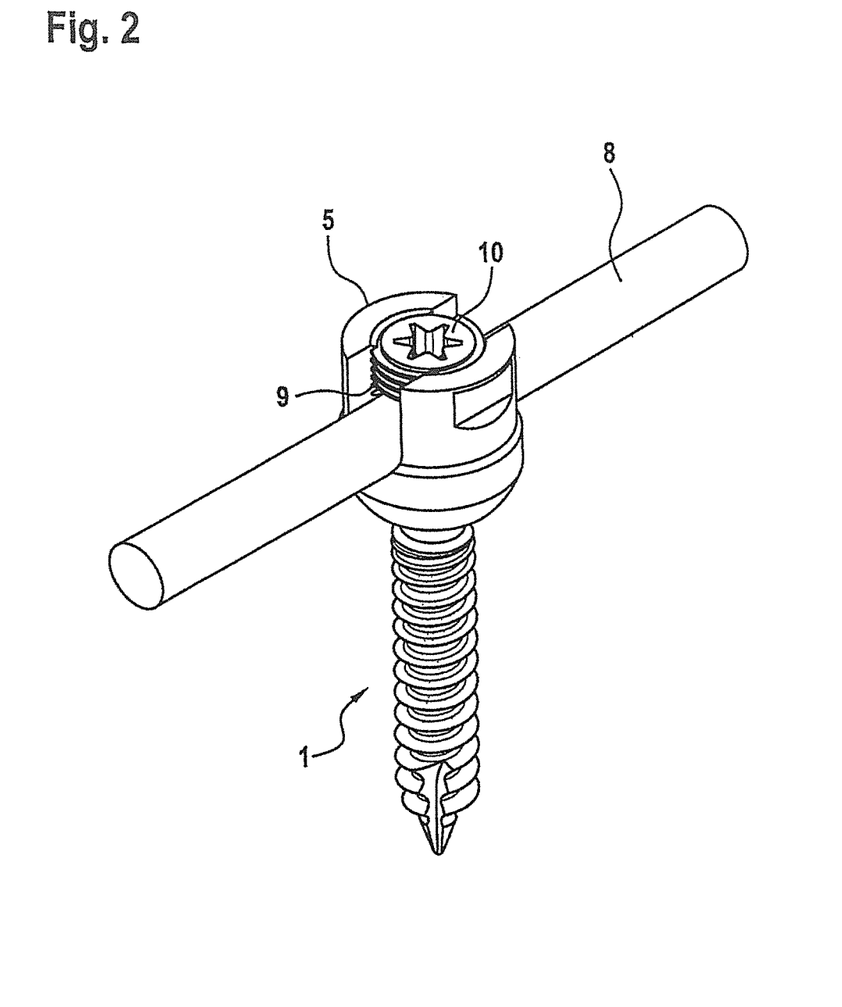
FIG. 2 shows a detailed view of a mounted state according to FIG. 1, FIGS. 3, 4 show sectional views in the mounted state, analogous to FIG. 2, FIGS. 5, 6 show a lateral sectional view as well as a front-side view of an exemplary embodiment of the safety screw according to the invention.
Figure 3:
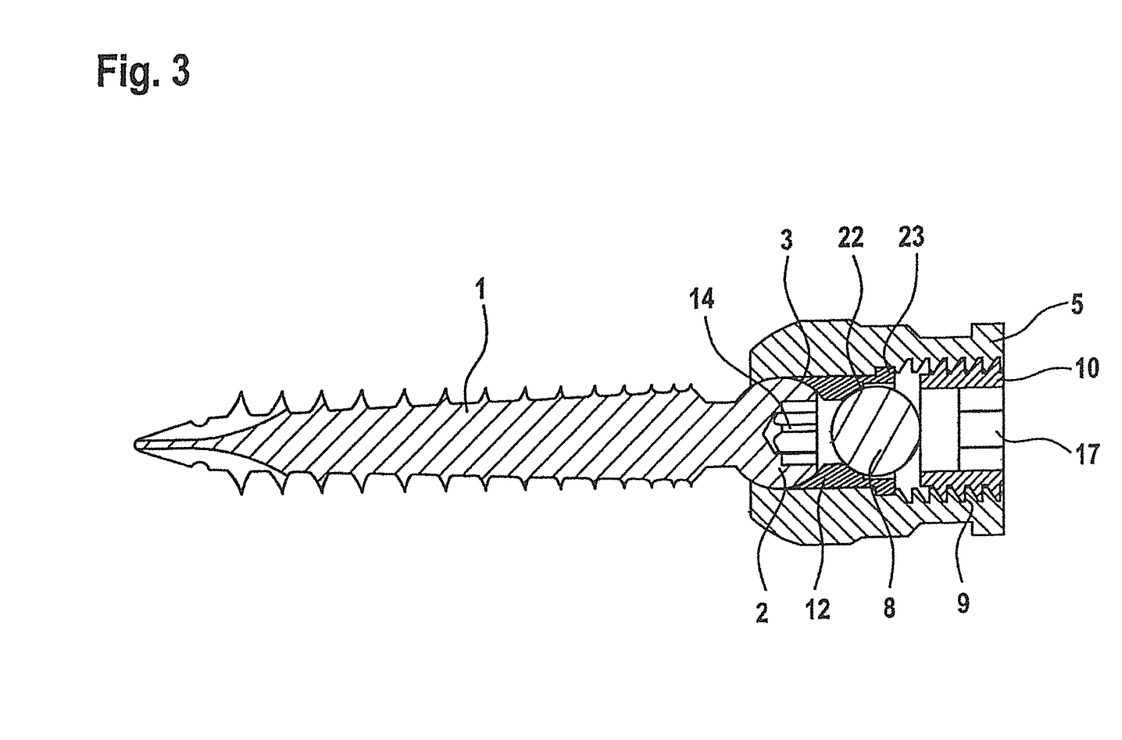
Figure 4:
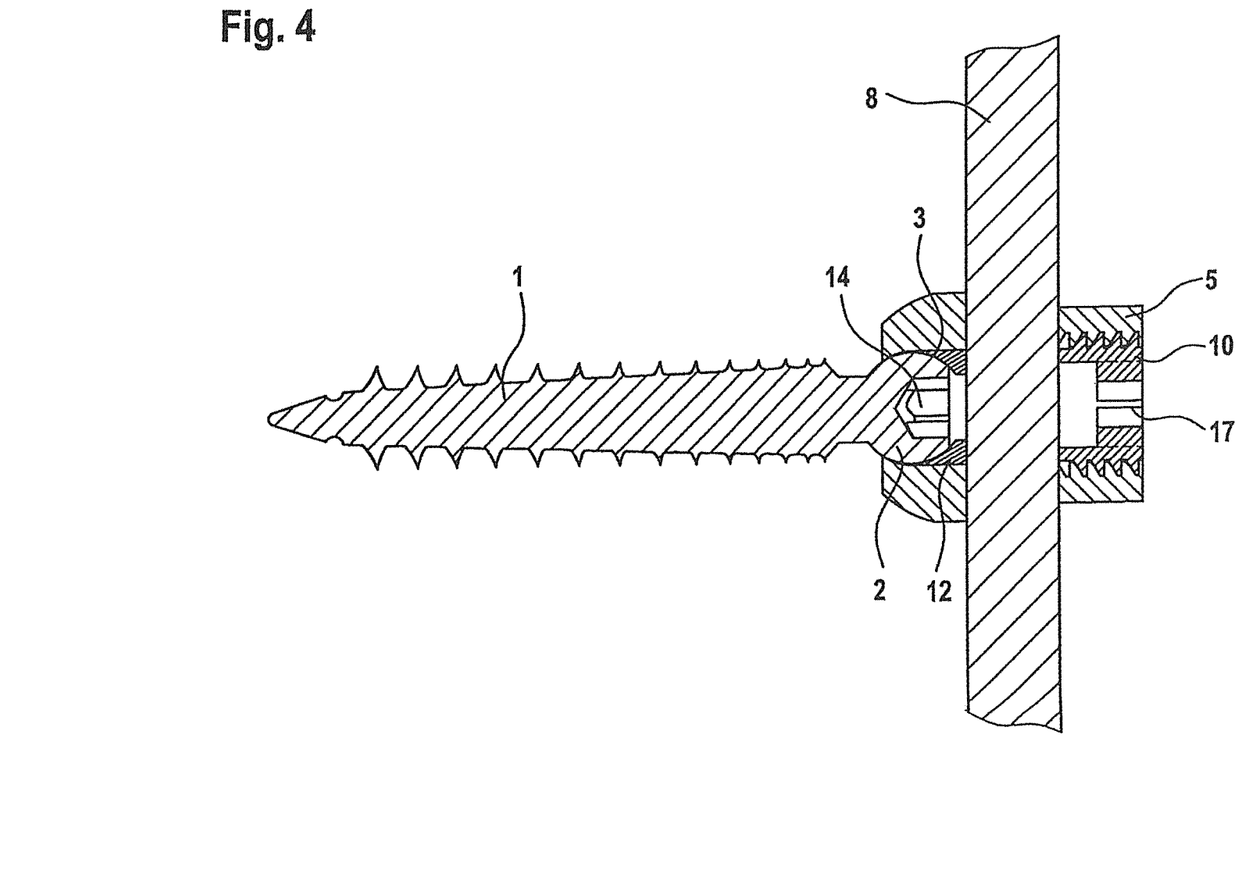
Figure 5:
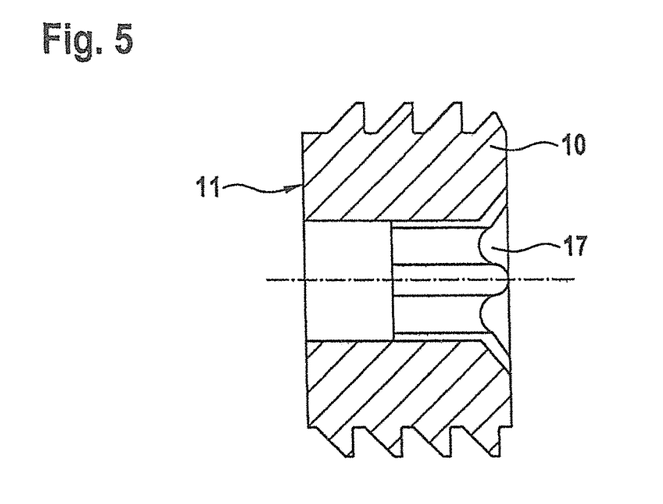

FIG. 2 shows an enlarged perspective rendering in the mounted state. From the renderings of FIGS. 3 and 4, which respectively illustrate an axial section along the longitudinal axis of the pedicle screw 4, the assignment of the individual structural components in the mounted state can be seen, wherein the views of FIGS. 3 and 4 are respectively rotated by 90° with respect to one another.

Figure 11:
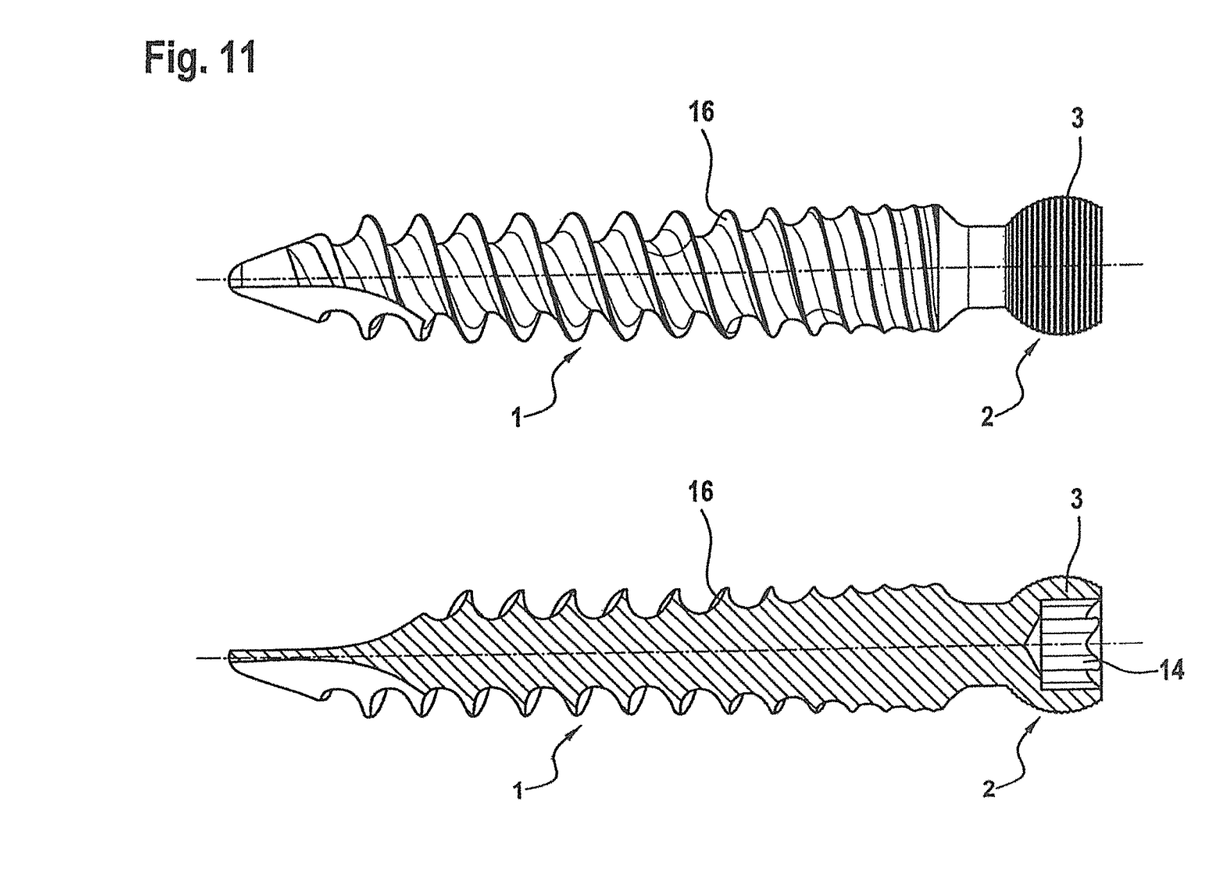
FIG. 11 shows a lateral view as well as a sectional view of a pedicle screw according to the invention.

At their head 2, the pedicle screws 1 have a tool meshing recess 14, also see FIG. 11. The thread is embodied as a compression thread and has a variable pitch in the conical core diameter as well as threaded tips of a consistent sharpness across the entire length of the screw. This can also be seen from the rendering of FIG. 11. The spherical area 3 of the head 2 is roughened up at its surface area, for example through circumferential furrows, or the like.

Figure 10:
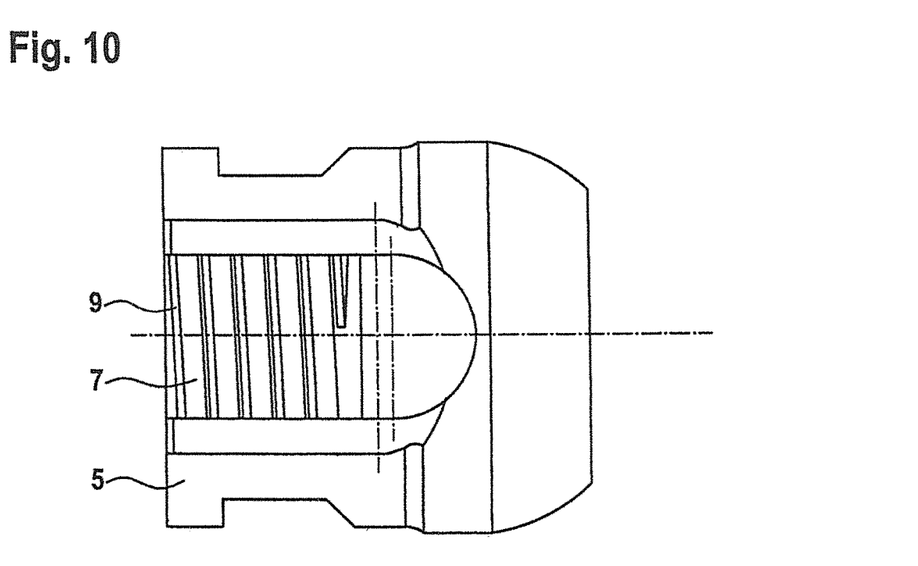

The pedicle screws 1, and particularly their heads 2, are passed through or stuck through the centric recess 6 of the pedicle head 4. The centric recess 6 of the pedicle head 4 is provided with a spherical mounting area 4, which is formed so as to match the spherical area 3 of the head 2 of the pedicle screw 1. Thus, the spherical area 3 abuts the spherical mounting area 4 with a full-area contact, whereby relative movements between the pedicle head 5 and the pedicle screw 1 are avoided in the clamped state. The design of the pedicle head 5 can particularly also be gathered from FIGS. 9 and 10. The slit 7 of the pedicle head 5 can be clearly seen in the frontal view of FIG. 9 (right hand rendering according to FIG. 9).

Figure 7:
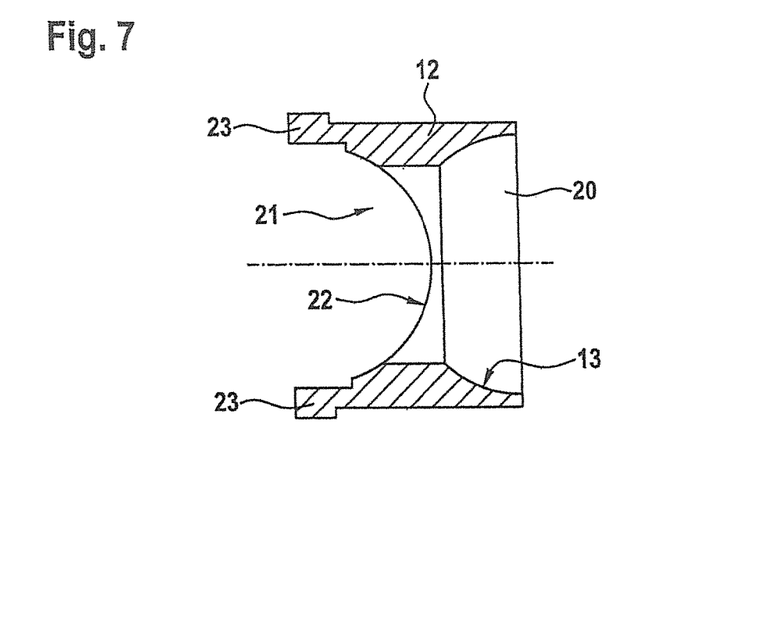
FIGS. 7, 8 show an axial sectional view as well as a lateral view of an exemplary embodiment of a safety sleeve according to the invention.
Figure 8:
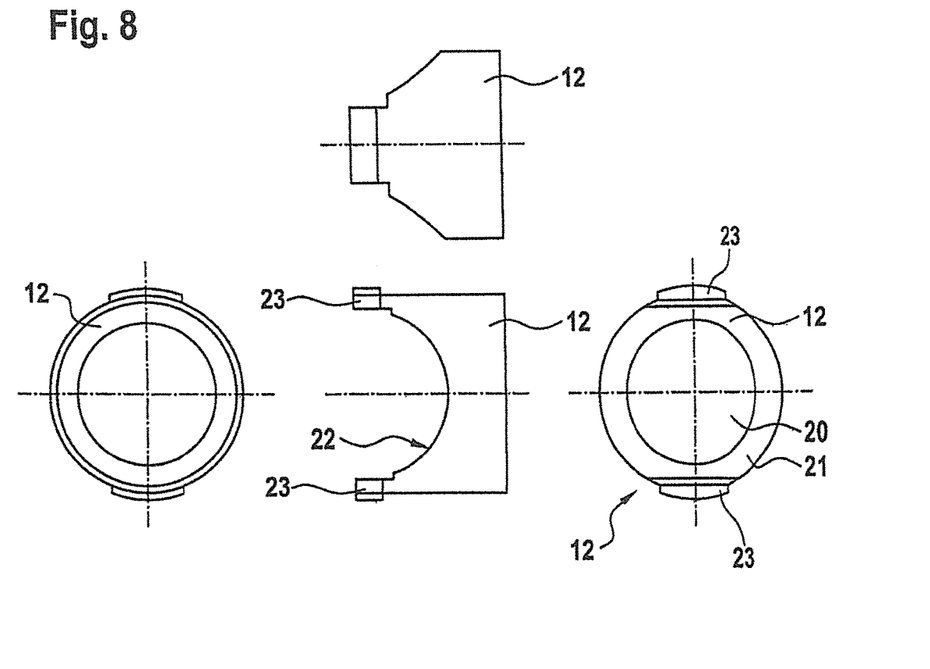

A safety sleeve 12 is arranged inside the centric recess 6, adjoining the head 2 of the pedicle screw 1, which will be explained in the following in connection with FIGS. 7 and 8.

A rod 8 is inserted into the slit 7, as can be seen from FIGS. 1 and 2. The rod 8 will be explained in more detail in the following in connection with FIGS. 19-25.

The safety screw 10 serves for clamping the rod 8 and is provided with a tool meshing recess 17, for example an internal polygon or an hexalobular internal profile.

At its front side that is facing towards the rod 8, the safety screw 10 is provided with an anti-rotation device 11. It comprises alternatingly arranged radial elevations 18 and radial concave areas 19. What thus results is a star-like design of the front side, see in particular FIGS. 6 and 12 to 18. The radial elevations 18 and the radial concave areas 19 are arranged in an alternating manner with respect to one another and result in a form-fit catching with the rod 8 when the safety screw 10 is screwed in.

Figure 6:
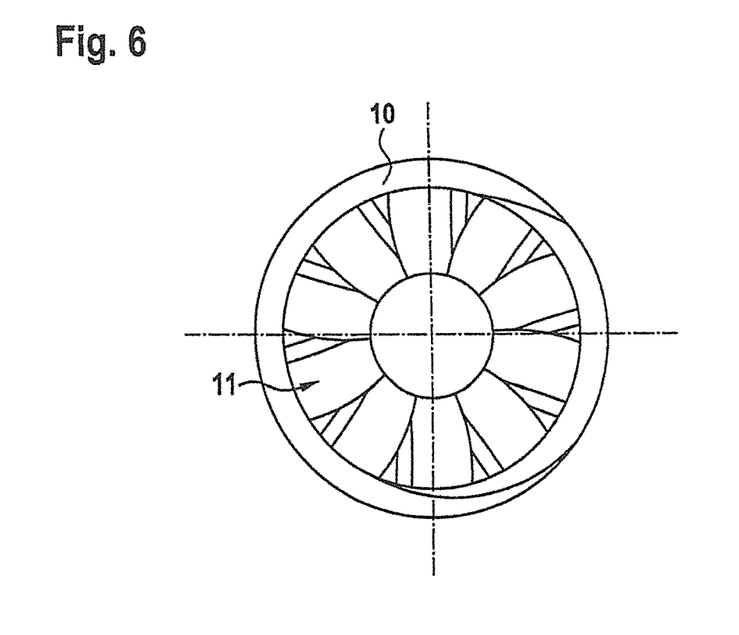
Figure 12:
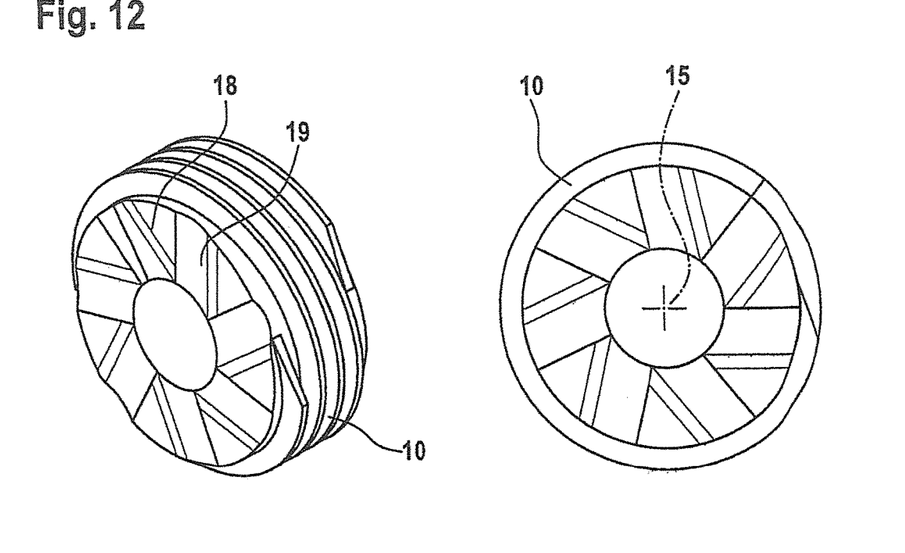
FIGS. 12-18 show perspective as well as front-side views of different exemplary embodiments of the safety screw according to the invention.
Figure 13:
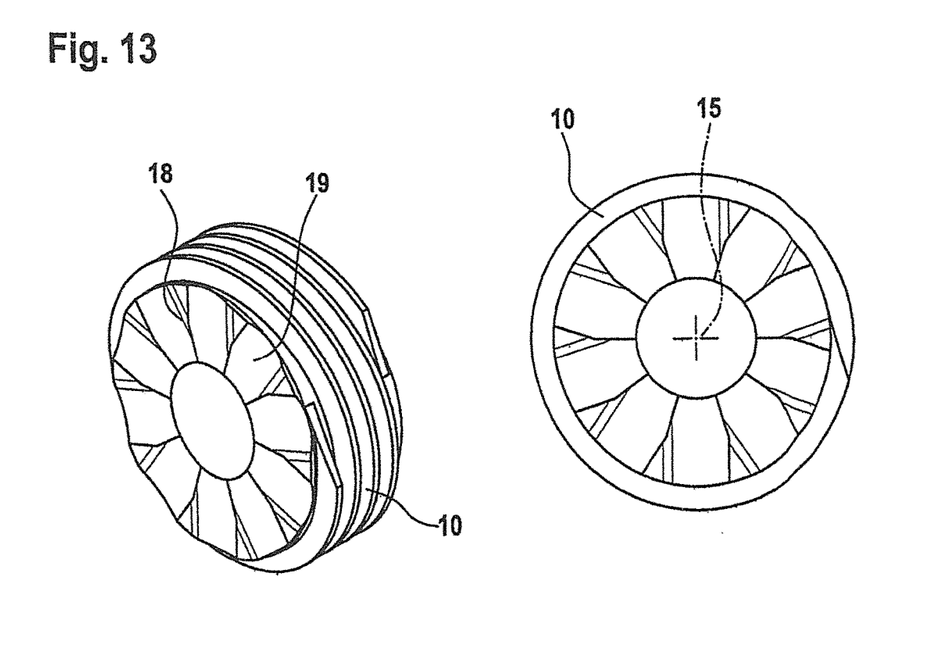
Figure 14:
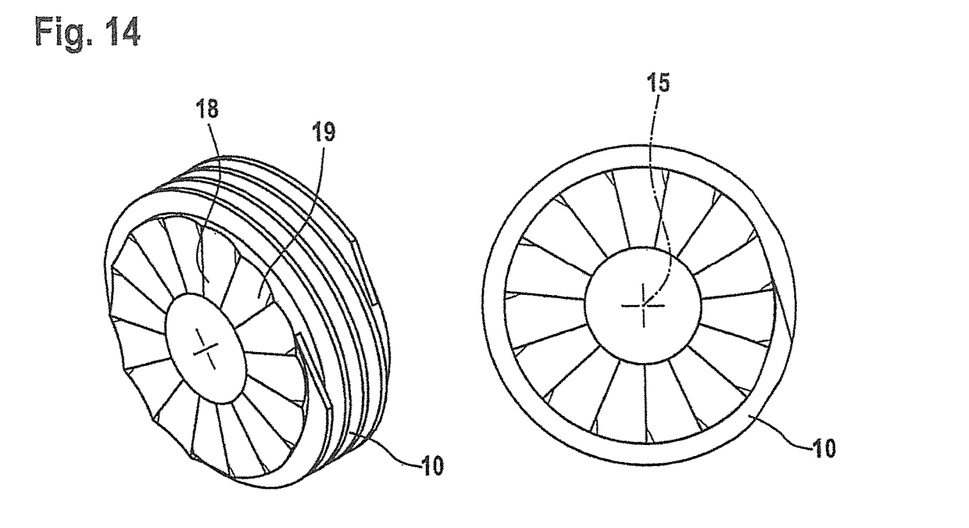
Figure 15:
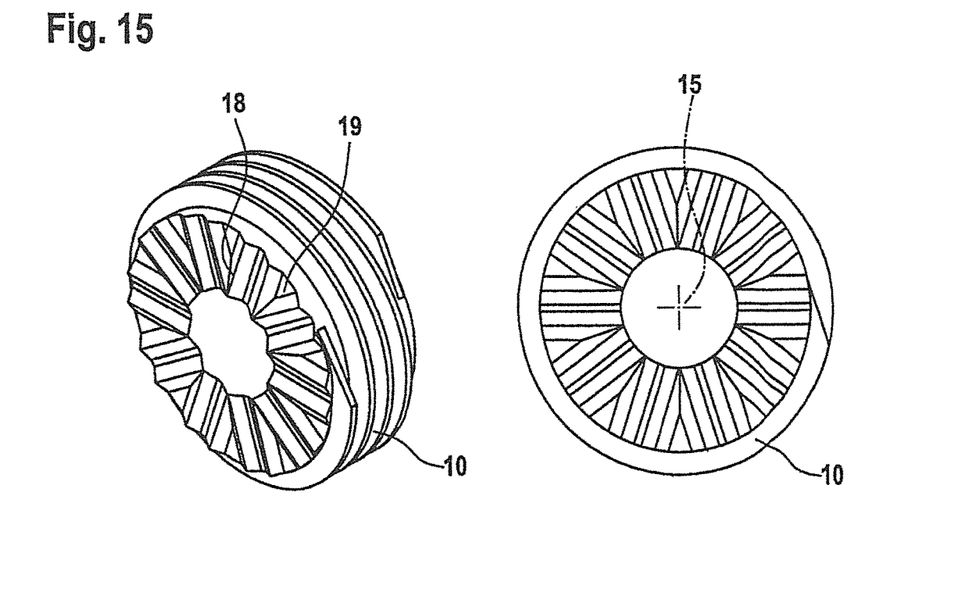
Figure 16:
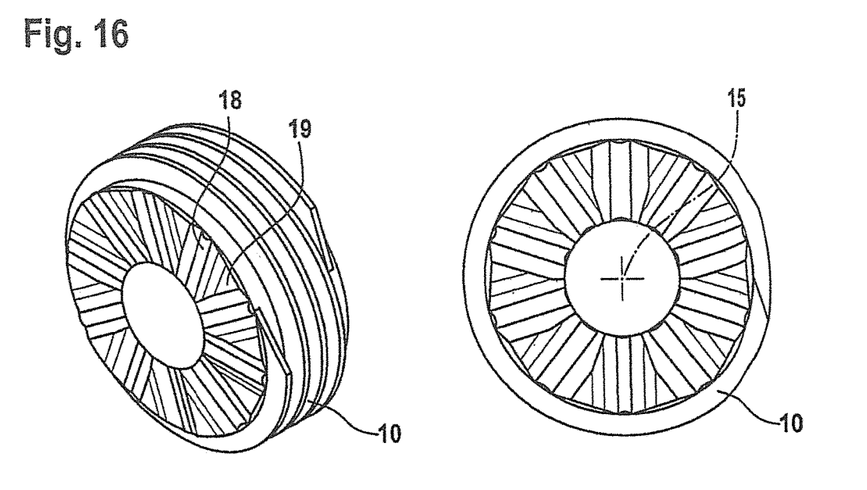
Figure 17:
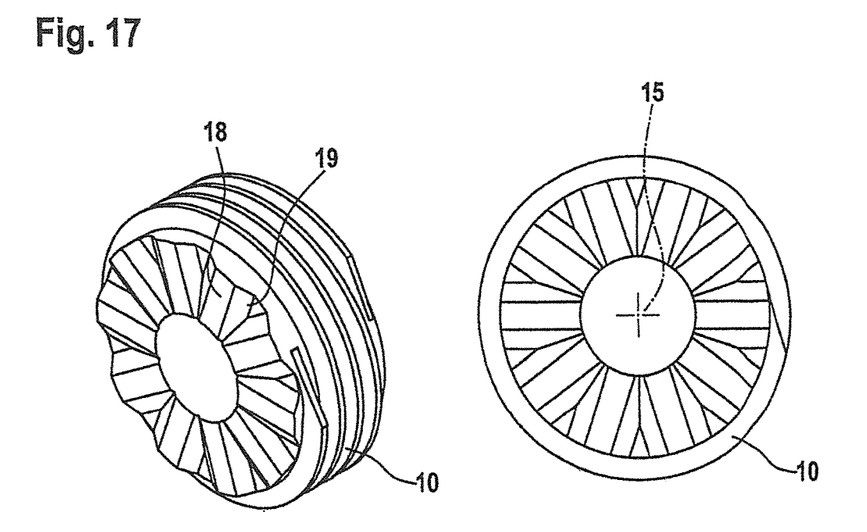
Figure 18:
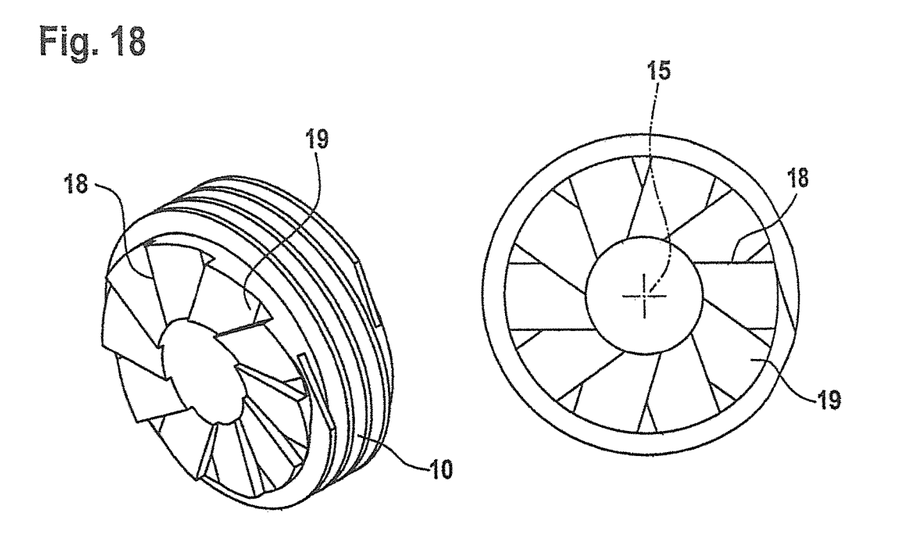

As follows from FIGS. 6 and 12 to 18, the anti-rotation device 11 can be embodied with different divisions. In the left hand rendering, FIGS. 12 to 18 respectively show a perspective view, and in the right hand rendering show a front-side view, analogous to FIG. 6. In FIG. 12, a division into 7 sections is provided, FIG. 6 shows a division into 10 sections, similar to FIG. 13. In FIG. 14, a division into 15 sections is provided. The radial elevations 18 and the radial concave areas 19 can be embodied in different manners, as can be seen in FIGS. 15-18. These exemplary embodiments show the radial elevations or radial concave areas 18, 19 in different cross-sectional embodiments, namely as a double triangle in FIG. 15, as a bulge-like embodiment in FIG. 16, with a trapezoid profile in FIG. 17, and with a chamfered profile having a triangular cross-section in FIG. 18. What thus results, with respect to the rotation of the safety screw 10 around its rotational axis 15, is a form-fit catching after the safety screw 10 has been fixated, which leads to the rod 8 being clamped in a secure manner.

In this manner, it is secured inside the pedicle head 5. At the same time, the axial pretension (with respect to the pedicle head 5) that is exerted on the rod 8 by the safety screw 10 leads to the head 2 of the pedicle screw 1 being clamped. The safety sleeve 12 described in FIGS. 7 and 8 serves for that purpose.

The safety sleeve 12 is inserted into the centric recess 6 of the pedicle head 5, as can also be seen from FIG. 3. As shown in FIGS. 7 and 8, the safety sleeve 12 has a centric recess 20 into which the rod 8 can be inserted. At the same time, the safety sleeve 12 is provided with a slit 21, which is provided with a substantially cylindrical area 22. The rod 8 can be inserted into the cylindrical area 22, so that it exerts a compression force on the safety sleeve 12 as the safety screw 10 is screwed in. That area of the safety sleeve 12 that is facing towards the head 2 of the pedicle screw 1 is provided with a spherical mounting area 13 (see FIG. 7) which is formed so as to match the spherical area 3 of the head 2 of the pedicle screw 1. This leads to the head 2 being clamped inside the pedicle head 5, so that no relative movement is possible between the pedicle head 5 and the head 2 of the pedicle screw 1.

At its end areas, the safety sleeve 12 is provided with snap-in noses 23 which snap into corresponding recesses 28 of the centric recess 6 of the pedicle head 5 in order to retain the pedicle head 5 at the pedicle screw 2 in such a manner that it is secured against loss after the pedicle screw 2 has been inserted, before the rod 8 is mounted in the further mounting process.

As follows from the synopsis of FIGS. 7, 8 and 3, the recesses 28 are formed as a part of an annular groove that is formed inside the wall of the centric recess 6 of the pedicle head 5. The snap-in noses 23 mesh with this annular groove. The snap-in noses 23 can be screwed into the ring-shaped recess 28 by rotating the safety sleeve 12 about its middle axis or the central axis of the pedicle head 5. In order to avoid any loosening of the snap-in noses 23 and any unintentional backtwisting of the safety sleeve 12, the wall of the recess 28 is provided with a structuring 29. The latter can be formed by areas of different radiuses and thus of different depths of the annular groove 28. Thus, the snap-in noses 23 catch with the structurings 29 when a rotation along the recess 28 takes place. In this way, the safety sleeve 12 is secured against any rotation.

As follows particularly from FIG. 3, the safety sleeve 12 is mounted inside the pedicle head 5 with some axial play, so that the safety sleeve 12 can be pretensioned inside the centric recess 6 of the pedicle head 5 against the spherical mounting area 3 of the head 2 of the pedicle screw 1 as the rod 8 is being pressed in by means of the safety screw 10 in order to tension the head 2 inside the pedicle head 5 in a manner secured against rotation.

Figure 19:
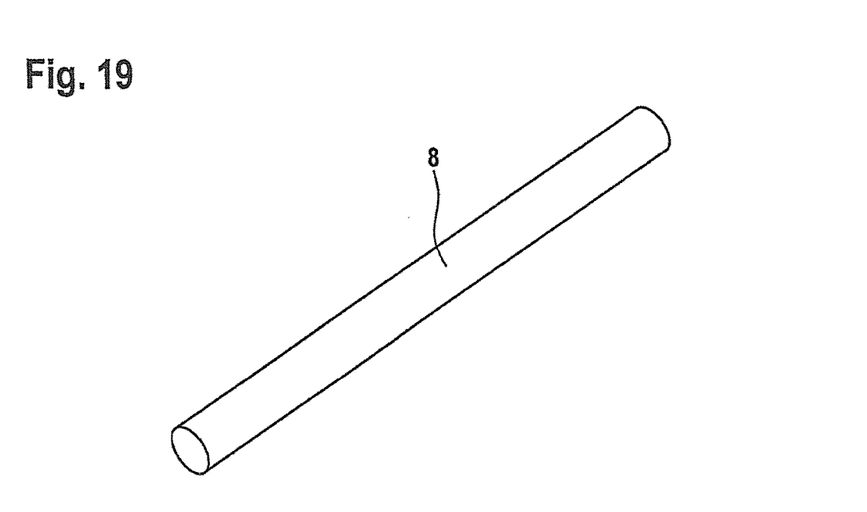
FIGS. 19-25 show perspective renderings of different embodiments of the rod according to the invention.
Figure 20:
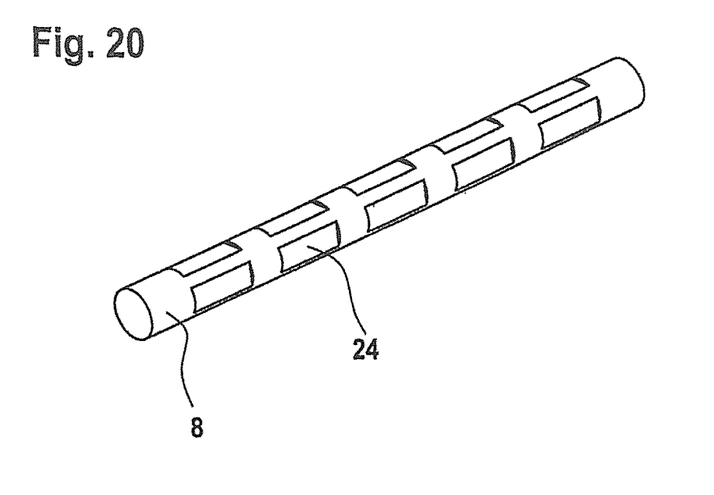
Figure 21:
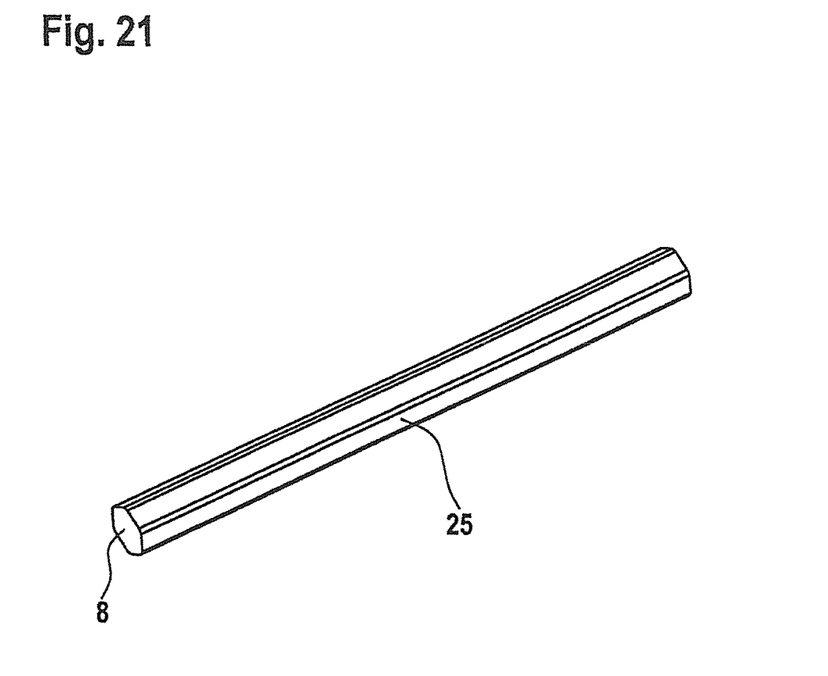
Figure 22:
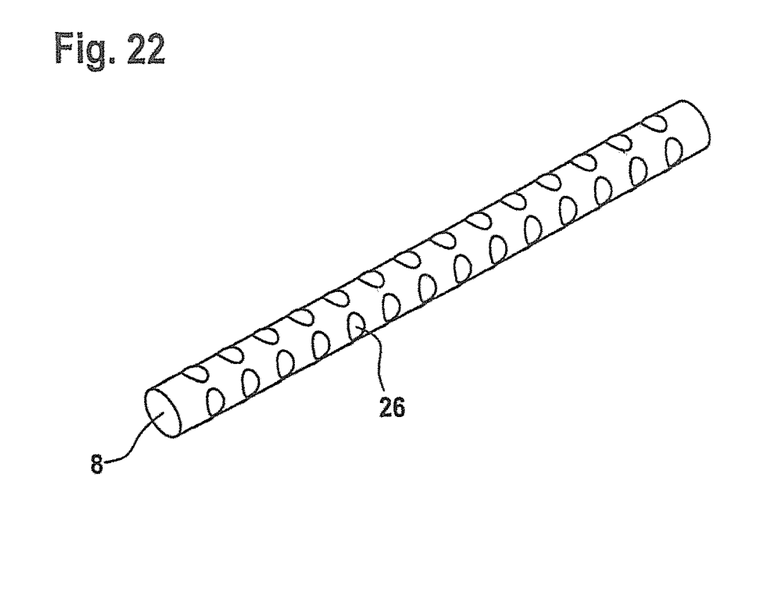
Figure 23:
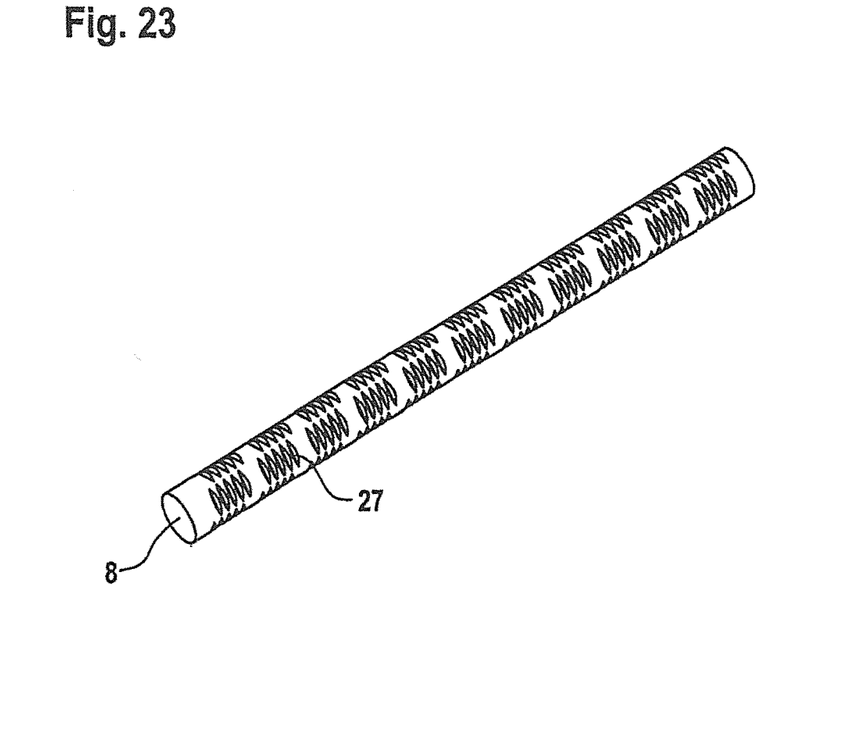
Figure 24:
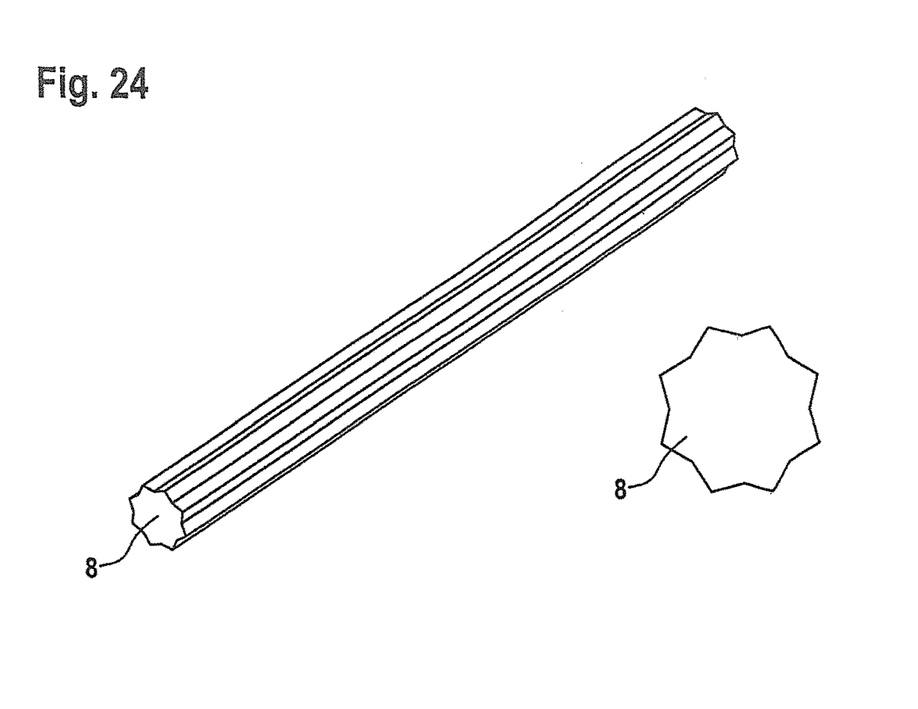
Figure 25:
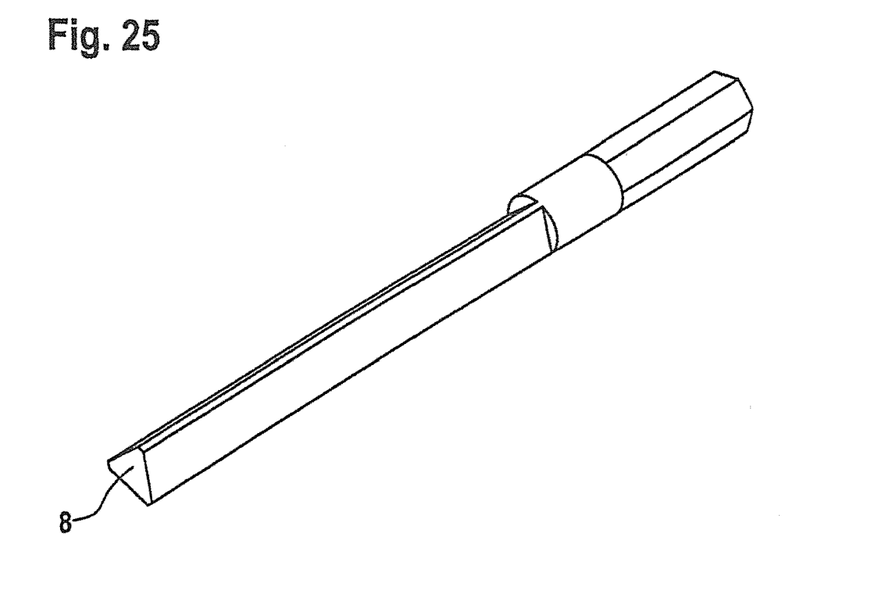

FIGS. 19-25 show different embodiments of the rod 8 according to the invention. It can be embodied in a smooth and cylindrical manner (FIG. 19). However, it is also possible to provide individual flattened surface segments 24, which are arranged so as to be distributed around the circumference and in the longitudinal direction of the rod 8 (FIG. 20). FIG. 21 shows an embodiment with continuous surfaces 25. FIG. 22 shows an exemplary embodiment in which spherical elements 26 are formed at the circumference of the rod 8. FIG. 23 shows a modification in which grilled segments 27 are provided. FIG. 28 shows an exemplary embodiment in which a profiled cross-section of the rod 8 is provided, see the right half of the image of FIG. 24. FIG. 25 shows an exemplary embodiment in which different cross-sections are provided, depending on the application site of the rod 8. According to the invention it is further possible to provide laser-modified surface area structures in any of the embodiments.

PARTS LIST

1 pedicle screw
2 head
3 spherical area
4 spherical mounting area
5 pedicle head
6 centric recess
7 slit
8 rod
9 internal thread
10 safety screw
11 anti-rotation device
12 safety sleeve
13 spherical mounting area
14 tool meshing recess
15 rotational axis
16 thread
17 tool meshing recess
18 radial elevation
19 radial concave area
20 centric recess
21 slit
22 cylindrical area
23 snap-in nose
24 surface segment
25 surface
26 spherical element
27 grilled segment
28 recess
29 structuring

The invention claimed is:

1. A device for bracing vertebrae of the human spinal column, comprising:
   a rod;
   a pedicle head including:
   a centric recess including an at least partially spherical mounting area,
   a slit for receiving the rod and positioning the rod transversally with respect to the centric recess,
   an internal thread which is formed inside the centric recess opposite the at least partially spherical mounting area;
   at least one pedicle screw including a head including a portion that is at least partially spherical and that is received inside the at least partially spherical mounting area;
   a safety screw engaging the internal thread for clamping the rod, wherein the safety screw includes an anti-rotation device at a side that faces towards the rod;
   a safety sleeve arranged inside the centric recess adjoining the head of the at least one pedicle screw, the safety sleeve including an at least partially spherical mounting area for engaging the at least partially spherical portion of the head of the at least one pedicle screw and axially securing the at least one pedicle screw inside the pedicle head, wherein the safety sleeve is clamped to the pedicle head;
   wherein the at least partially spherical portion of the head of the at least one pedicle screw includes a surface area that engages with the safety sleeve that is at least one chosen from structured and roughened;
   wherein the anti-rotation device engages the rod in a form-fit meshing.

2. The device according to claim 1, wherein the anti-rotation device includes radial elevations and radial concave areas.

3. The device according to claim 1, wherein a front-end side of the safety screw that faces towards the rod includes radial elevations—as viewed with respect to a rotational axis of the safety screw—that have a cross-section which is rounded to be bulging.

4. The device according to claim 1, wherein a front-end side of the safety screw that faces towards the rod includes radial elevations—as viewed with respect to a rotational axis of the safety screw—that have a trapezoidal cross-section.

5. The device according to claim 1, wherein a front-end side of the safety screw that faces towards the rod includes radial elevations—as viewed with respect to a rotational axis of the safety screw—that have a chamfered cross-section.

6. The device according to claim 1, wherein a front-end side of the safety screw that faces towards the rod includes radial elevations—as viewed with respect to a rotational axis of the safety screw—that have a triangular cross-section.

7. The device according to claim 1, wherein the head of the at least one pedicle screw includes a tool meshing recess that is accessible through the centric recess of the pedicle head and through the safety sleeve.

8. The device according to claim 1, wherein the rod includes a surface area that is smooth.

9. The device according to claim 1, wherein the rod includes a surface area that is roughened.

10. The device according to claim 1, wherein the rod includes a surface area that includes a structured surface.

11. The device according to claim 10, wherein the structured surface includes flattened areas.

12. The device according to claim 10, wherein the structured surface includes semi-spherical elements.

13. The device according to claim 10, wherein the structured surface includes grilled segments.

14. The device according to claim 10, wherein the structured surface includes a polygonal cross-section.

\* \* \* \* \*